United States Patent [19]

Sugihara et al.

[11] Patent Number: 5,787,525

[45] Date of Patent: Aug. 4, 1998

[54] LAYERED FABRIC MATTRESS

[75] Inventors: Toshio Sugihara; Mitsuo Suzuki; Marcos Masaki Komiya, all of Tokyo-to, Japan

[73] Assignee: Life Energy Industry Inc., Japan

[21] Appl. No.: 678,061

[22] Filed: Jul. 9, 1996

[51] Int. Cl.$^6$ .................................................. A47C 21/04
[52] U.S. Cl. ................................... 5/421; 5/690; 5/952
[58] Field of Search ............................... 5/482, 421, 952, 5/948, 690; 428/323, 325; 442/375, 417

[56] References Cited

U.S. PATENT DOCUMENTS

| | | | |
|---|---|---|---|
| 2,013,562 | 9/1935 | Karr | 5/690 |
| 2,455,468 | 12/1948 | Theodore | 5/421 |
| 3,624,312 | 11/1971 | Koukal et al. | |
| 3,900,648 | 8/1975 | Smith | 5/952 |
| 3,924,284 | 12/1975 | Nelson | 5/690 |
| 4,423,308 | 12/1983 | Callaway et al. | 5/421 |
| 4,680,822 | 7/1987 | Fujino et al. | 5/421 |
| 4,825,868 | 5/1989 | Susa et al. | 5/421 |
| 5,329,096 | 7/1994 | Suematsu | 5/421 |
| 5,501,891 | 3/1996 | Saika et al. | 5/901 |

FOREIGN PATENT DOCUMENTS

| | | |
|---|---|---|
| 2169764 | 6/1990 | Japan . |
| 4327207 | 11/1992 | Japan . |
| 8205968 | 8/1996 | Japan . |
| 2187113 | 9/1987 | United Kingdom ............... 5/952 |

*Primary Examiner*—Steven N. Meyers
*Assistant Examiner*—Tuye T-Phuong Pham
*Attorney, Agent, or Firm*—Wenderoth, Lind & Ponack, L.L.P.

[57] ABSTRACT

Proposed is a fabric mattress having a layered structure as a kind of health-promoting bedding goods, which comprises an upper fabric layer, a lower fabric layer and an intermediate fabric layer sandwiched between the upper and lower fabric layers, at least a part of these fabric layers being formed from fibers such as rayon fibers containing very fine particles of tourmaline in an amount of up to 7% by weight. This unique ingredient in the fibers has an effect to emit active electrons and far-infrared light which exhibit an invigorating effect on the human body cells of the person lying on the mattress to promote blood circulation so that even a patient lastingly lying on the bed never suffers from bedsores by using the mattress which can be constructed to have good air permeation.

14 Claims, 9 Drawing Sheets

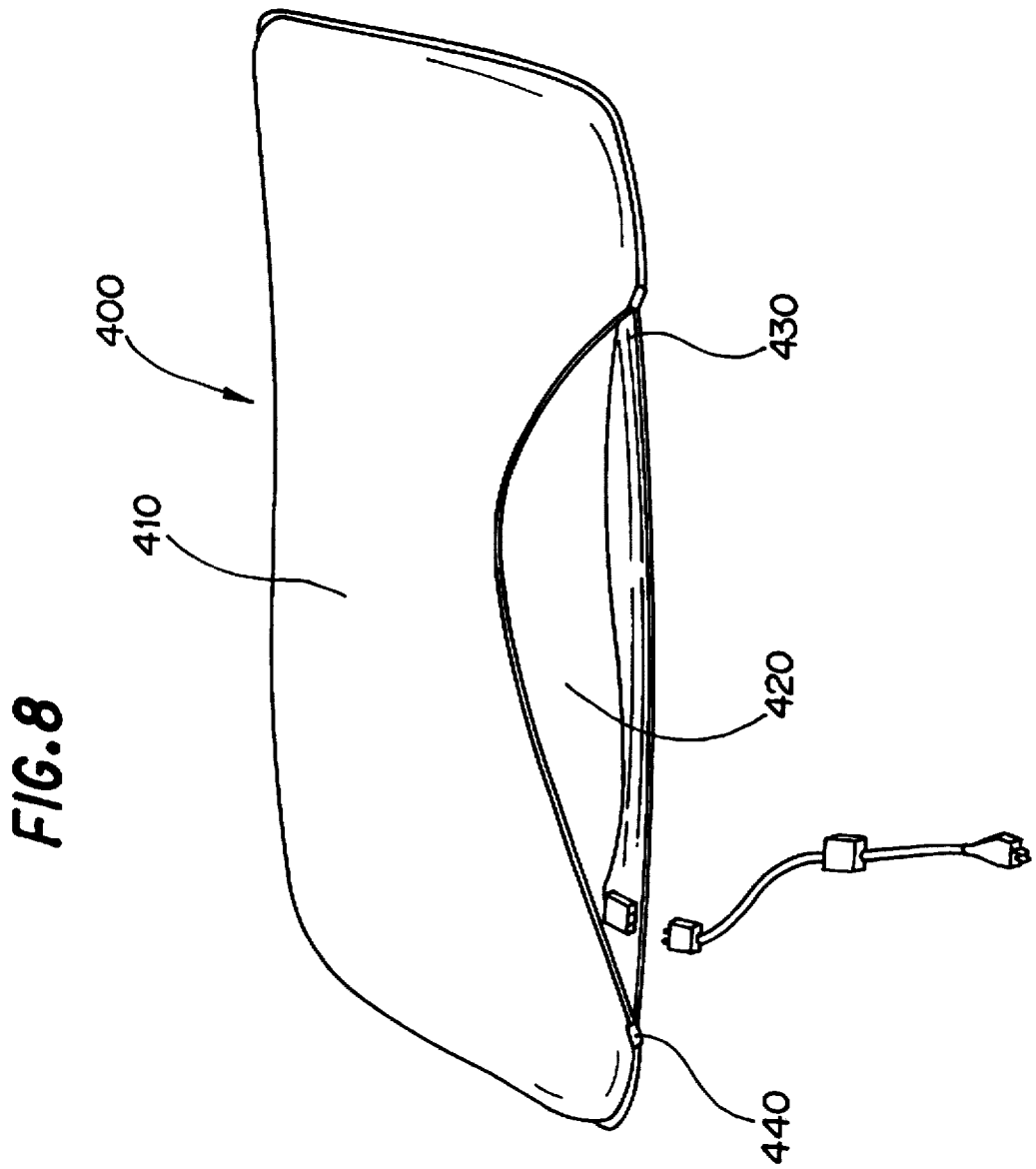

LAYERED FABRIC MATTRESS

BACKGROUND OF THE INVENTION

The present invention relates to a novel layered fabric mattress or, more particularly, to a layered fabric mattress capable of exhibiting a cell-invigorating effect on the human body in contact therewith or lying thereon.

The inventors previously proposed electret fibers which exhibit a promoting effect on the metabolism of and blood circulation in a human body in contact therewith by virtue of the synergism of the electric stimulation to the human body by the active electrons emitted therefrom and the far-infrared emission at the human skin so as to be useful in the therapeutic treatment of patients suffering from oversensitivity to cold and stiffness in the shoulders as well as for the purpose of aging retardation for aged people and health promotion of normal people (see Japanese Patent Kokai 4-327207 and Japanese Patent Publication 6-104926).

SUMMARY OF THE INVENTION

The present invention has an object to provide a novel layered fabric mattress as a kind of bedding goods for health-promotion by exhibiting a invigorating effect on the cells of a human body in contact therewith or lying thereon by virtue of release of active electrons and emission of far-infrared light by which the human body cells are stimulated resulting in promotion of the blood circulation and improvement of the human body metabolism.

Thus, the layered fabric mattress of the present invention is a layered composite body which comprises:

two fabric surface sheets; and an intermediate fabric batting sheet stuffing the space between the two fabric surface sheets, at least one of the two fabric surface sheets and the intermediate fabric batting sheet consisting of fibers containing particles of tourmaline or, generally, an electret mineral.

In particular, it is preferable that the tourmaline particles are contained in the fibers constituting the batting sheet, which is preferably a non-woven fabric sheet.

BRIEF DESCRIPTION OF THE DRAWING

FIG. 8 is a perspective view of a mattress of the invention with a built-in heater in a demountable fashion.

DETAILED DESCRIPTION OF THE PREFERRED EMBODIMENTS

Figure 1:
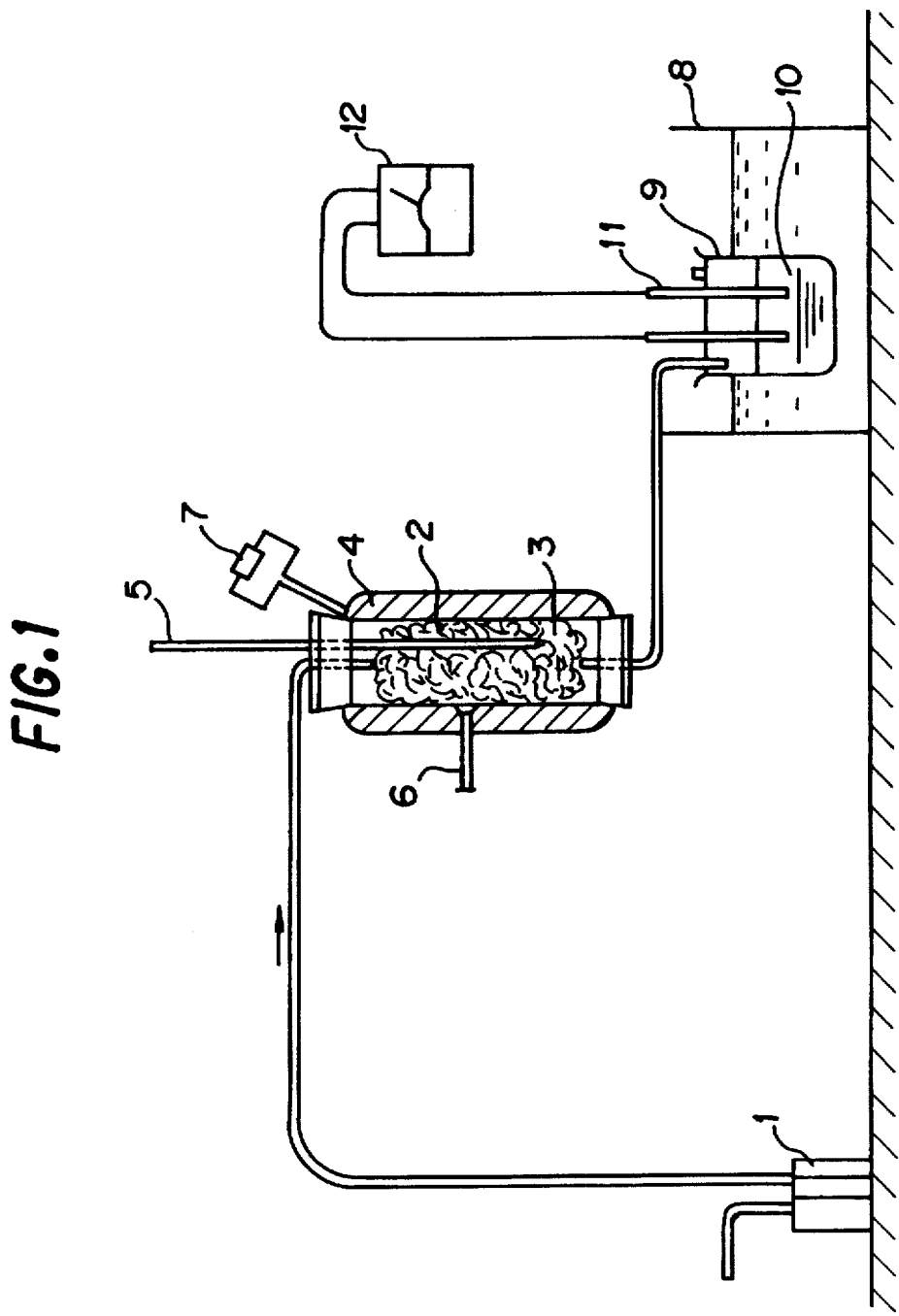
FIG. 1 is a schematic illustration of the apparatus system for the investigation of the changes in the electric conductivity of water by the active electrons released from tourmaline-containing rayon fibers.

As is described above, the layered fabric mattress of the present invention is a kind of health-promoting goods as an application of so-called electret fibers. Namely, the inventive layered fabric mattress comprising fibers containing particles of an electret mineral such as tourmaline has an effect to invigorate the human body cells of a person lying thereon with improvement of the blood circulation by virtue of the release of active electrons and emission of far-infrared light from the tourmaline-containing fibers. The electret mineral above mentioned is a dielectric mineral in which a permanent state of electric polarization has been set up. Various kinds of electret minerals are known in the art including tourmaline, serpentinite, amphibole, quartz, granite and the like, of which tourmaline is preferred in the invention. The amount of the active electrons released therefrom can be increased by the movement of the human body lying on the mattress to give a dynamic energy to the tourmaline-containing fibers to exhibit a piezoelectric effect. The amount of the active electrons released from the mattress can also be increased by the pyroelectric effect induced when the mattress is exposed to sunlight or the mattress is internally heated by means of an electric heater built therein.

The mattress of the invention can be so thin and so light that the mattress can be laundered as a whole if the mattress has no built-in heater or the built-in heater thereof is detached therefrom.

When the batting layer of the mattress formed from tourmaline-containing fibers is constructed to have a three-dimensional structure such as a honeycomb structure, the inventive mattress can be imparted with good air-permeability and dryability so that a patient prolongedly lying on a bed using the inventive mattress can be exempted from bedsores by virtue of the dispersion of the body weight over a wide area synergistically with the effect of air-permeation and rapid drying to produce an adverse condition against propagation of bedsore-causing microorganisms.

The batting layer can be a non-woven fabric sheet which is advantageous over woven fabrics because the content of the tourmaline particles contained in the fibers can be increased so much as to substantially increase the release of active electrons.

When the batting layer is a composite consisting of a tourmaline-containing non-woven fabric sheet and a layer of a three-dimensional honeycomb structure, the mattress, on which a person lies, can be used in a cold season with the former layer in proximity of the human body so that the feeling of warmness can be enhanced by the non-woven fabric layer while, in a hot season, the mattress can be used with the latter layer in proximity of the human body so that the person lying thereon can be freed from the unpleasant feeling of stuffiness due to accumulation of moisture by virtue of the good air permeability and dryableness of the latter layer.

Tourmaline, which is incorporated into fibers in the form of fine particles, is a mineral having a chemical composition expressed by the formula

$MX_3B_3Al_3(AlSi_2O_9)_3(O, OH, F)_4$, in which M is sodium or calcium and X is an element or combination of elements selected from the group consisting of aluminum, iron, lithium, magnesium and manganese.

Crystals of tourmaline having a high purity can be used as a kind of gem stones and, while a synthetic method for the preparation of tourmaline crystals has been established, naturally occurring and synthesized tourmaline minerals can equally be used in the invention. Tourmaline is known as a substance exhibiting permanent spontaneous electric polarization and the vector of the polarization is not affected by an external electric field. It is also known that the permanent polarization exhibited by a tourmaline crystal is the strongest among minerals and far-infrared light is emitted therefrom. It is also known that a crystal of tourmaline exhibits the piezoelectric effect, which is a phenomenon of dielectric polarization exhibited by a certain ionic crystal under stress by an external force, and the pyroelectric effect, which is a phenomenon to cause appearance of electric charges on the surface of a crystal when the crystal is locally heated. It is already confirmed by experiments that active electrons are released from fibers containing fine particles of tourmaline.

The spontaneous permanent polarization exhibited by a crystal of tourmaline is more remarkable when the crystal is in the form of very fine particles. It is preferable in the present invention that the particles to be incorporated into fibers have a particle diameter not exceeding 2.0 μm or, more preferably, not exceeding 0.5 μm or, most preferably, not exceeding 0.3 μm. The phenomenon of active electron emission can be most remarkable when the tourmaline particles have a particle diameter not exceeding 0.2 μm with an average particle diameter not exceeding 0.1 μm.

The amount of the tourmaline particles incorporated into fibers is in the range from 0.05 to 7.0% by weight based on the unloaded fibers. When the amount of the tourmaline particles is too small, the amount of active electrons emitted from the fibers would be too small so that the desired advantages in the present invention cannot be accomplished as a matter of course while no particular additional advantages can be obtained by increasing the amount thereof to exceed the above mentioned upper limit rather with an economical disadvantage along with a decrease in the fiber strength. When the balance between the active-electron emissivity and the economical merit is taken into consideration, the amount of tourmaline particles is selected in the range from 0.05 to 2.0% by weight based on the amount of the unloaded fibers.

It is optional that, besides the tourmaline particles, the fibers are incorporated with fine particles of other inorganic materials such as alumina, siliceous minerals, e.g., cordierite and β-spodumene, zirconia, zircon, magnesia, aluminum titanate and the like known as a far-infrared emitting material as well as oxides of a transition metal element such as manganese dioxide, iron oxide, chromium oxide, cobalt oxide and copper oxide and synthetic ceramic materials such as silicon nitride and silicon carbide in an amount not exceeding 10% by weight based on the amount of unloaded fibers.

Various kinds of fibers can be incorporated with tourmaline particles including regenerated fibers such as viscose rayon and cuprammonium rayon, semi-synthetic fibers such as cellulose acetate and fibers of synthetic resins such as polyesters, polyurethanes, polyamides, polyvinyl chlorides, polyvinyl alcohols and polyacrylonitriles without particular limitations.

The non-woven fabric sheet consisting of the tourmaline-containing fibers to be used for the batting sheet of the inventive layered fabric mattress can be prepared by the span-bond method, melt-blow method and the like. It is of course optional that the non-woven fabric sheet is formed from the tourmaline-containing fibers alone or from an intertwinement of the tourmaline-containing fibers and plain fibers without tourmaline particles.

In the following, the layered fabric mattress of the invention is described in more detail by way of examples.

EXAMPLE 1

(1) Preparation of tourmaline-containing rayon fibers

According to the conventional viscose process, 100 parts by weight of a cellulose pulp were admixed with 350 parts by weight of a 20% aqueous solution of sodium hydroxide and the blend was agitated for 2 hours at room temperature to give an alkali cellulose which was admixed with 30 parts by weight of carbon disulfide and agitated for 3 hours at room temperature to give a solution of cellulose sodium xanthate. By diluting the thus obtained xanthate solution with an aqueous alkaline solution, a master spinning solution was prepared, of which the content of cellulose was 8.7% by weight, total alkali content was 6.0% by weight and total sulfur content was 2.4% by weight.

The master spinning solution was uniformly admixed with fine particles of tourmaline prepared by the water-granulation method and having a particle diameter not exceeding 0.2 μm with an average particle diameter of 0.15 μm in amounts of 0.05%, 0.1%, 0.2%, 0.3%, 0.5%, 1.0%, 2.0%, 3.0% , 5.0% and 7.0% by weight to give a tourmaline-containing spinning solution.

Each of the thus prepared spinning solutions containing tourmaline particles was subjected to spinning at 50° C. by using a spinnerette having 50 openings of 0.08 mm diameter at a spinning velocity of 60 meters/minute into a spinning bath of an aqueous solution containing 120 g/liter of sulfuric acid, 280 g/liter of sodium sulfate and 15 g/liter of zinc sulfate followed by a drawing treatment in a conventional two-bath stretch spinning method to give tourmaline-containing rayon fibers, referred to as the fibers No. 1 to No. 10, respectively, having a fineness of 15 denier.

(2) Test for emission of active electrons from tourmaline-containing fibers

Emission of active electrons from the tourmaline-containing fibers was investigated by means of the changes in the electric conductivity of water blown with air after passing through a bed of the tourmaline-containing fibers by using the apparatus system schematically illustrated in FIG. 1 in a procedure described below. The sample of tourmaline-containing rayon fibers prepared as above was mounted on the sample mount 3 installed inside of the activation vessel 2. The blower pump 1 was operated to introduce clean air freed from carbon dioxide and the like into the activation vessel 2 at a rate of 100 ml/minute while keeping the sample fibers on the sample mount 3 at a temperature of 35° C. by means of a ceramic heater 4 under power supply from the power source 7 and surrounding the activation vessel 2 which was equipped with a thermometer 5 and a temperature sensor 6 to facilitate temperature control.

Figure 2:
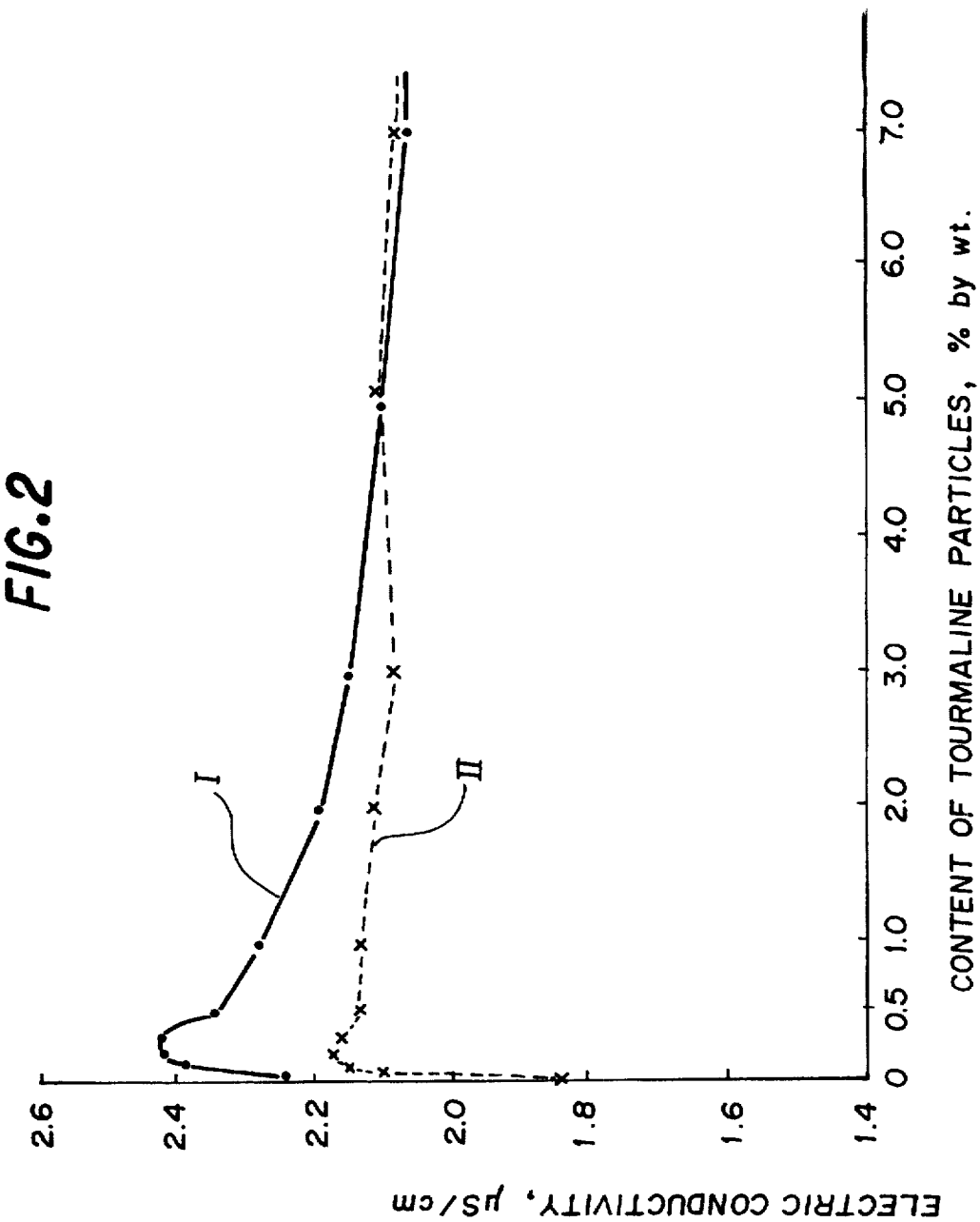
FIG. 2 is a graph showing the change in the electric conductivity of water by the active electrons released from tourmaline-containing fibers.

The air permeating the sample mount 3 was blown at the surface of the distilled water 10 at 21° C., of which the initial conductivity was 1.7 μS/cm at 21° C., in a glass beaker 9 held in a thermostat 8. The change in the conductivity of the water 10 was monitored with a conductivity meter 12 (Precision LCR Meter, Model 4285A, manufactured by Hewlett-Packard Co.) by means of the rod-formed platinum electrodes 11 inserted into the water 10. Table 1 below gives the value of the conductivity of the distilled water 10 after three hours of continued blowing of the air at the surface of water for the fiber samples No. 1 to No. 10 containing varied amounts of the tourmaline particles having a particle diameter not exceeding 0.2 μm in the range from 0.05% to 7.0% by weight. The conductivity of the water after three hours of air blowing is graphically shown as a function of the content of the tourmaline particles in the rayon fibers by the curve I of FIG. 2.

EXAMPLE 2

The experimental procedure was substantially the same as in Example 1 except that the tourmaline particles incorporated into the rayon fibers had a particle diameter not exceeding 1.0 μm with an average particle diameter of 0.8 μm in place of the finer tourmaline particles used in Example 1. The values of the conductivity of the distilled water after three hours of air blowing are shown for the samples No. 11 to No. 21 containing varied amounts of the tourmaline particles, sample No. 11 being for the purpose of control with the rayon fibers containing no tourmaline particles. The conductivity of the water after three hours of air blowing is graphically shown as a function of the content of the tourmaline particles in the rayon fibers by the curve II (broken line curve) of FIG. 2.

TABLE 1

|  |  | Example 1 |  | Example 2 |  |
| --- | --- | --- | --- | --- | --- |
|  |  | Fiber sample No. | Conductivity, μS/cm | Fiber sample No. | Conductivity, μS/cm |
| Content | 0 | — | — | 11 | 1.84 |
| of | 0.05 | 1 | 2.24 | 12 | 2.10 |
| tourmaline | 0.1 | 2 | 2.39 | 13 | 2.15 |
| particles, | 0.2 | 3 | 2.42 | 14 | 2.17 |
| % by | 0.3 | 4 | 2.42 | 15 | 2.16 |
| weight | 0.5 | 5 | 2.34 | 16 | 2.13 |
|  | 1.0 | 6 | 2.28 | 17 | 2.13 |
|  | 2.0 | 7 | 2.19 | 18 | 2.11 |
|  | 3.0 | 8 | 2.15 | 19 | 2.08 |
|  | 5.0 | 9 | 2.10 | 20 | 2.10 |
|  | 7.0 | 10 | 2.06 | 21 | 2.08 |

As is understood from these experimental results, the electric conductivity of the distilled water was increased to 2.08 to 2.17 μS/cm after three hours of air blowing at the surface of water when the air was passed through a bed of the tourmaline-containing rayon fibers as compared with the control with rayon fibers containing no tourmaline particles giving a conductivity of water of 1.84 μS/cm. These results support the conclusion that a large amount of active electrons are emitted from the tourmaline-containing rayon fibers and carried by the air stream to be introduced into the distilled water. This effect could be obtained with only 0.05% by weight of the content of tourmaline particles in the rayon fibers and increase in the amount up to 2.0% by weight had almost no additional effect with the conductivity of water without any further increase.

This is in contrast with the results obtained in Example 1 using finer tourmaline particles, in which the conductivity of water was maximum at the content of tourmaline particles of 0.2 to 0.3% by weight and decreases when the content of the tourmaline particles in the rayon fibers was decreased or increased although the peak value of the conductivity of water much higher than in Example 2 indicating more intense emission of active electrons from the finer tourmaline particles.

Further, the sample fibers No. 3 and No. 9 containing 0.2% by weight and 5.0% by weight, respectively, of the tourmaline particles were examined with a high-resolution transmission electron microscope (Model JEM-200CX, manufactured by Nippon Denshi Co.) at an acceleration voltage of 160 kV to find that the fibers of the sample No. 3 contained uniformly dispersed tourmaline particles having a particle diameter in the range from 0.02 to 0.2 μm mostly distributing in the range smaller than 0.1 μm. In contrast thereto, the fibers of the sample No. 9 contained agglomerated particles having a particle diameter mostly distributing in the range from 0.2 to 1.8 μm formed by agglomeration of the tourmaline particles having a particle diameter not exceeding 0.1 μm. This result of the electron microscopic examination indicates that a very uniform dispersion of the tourmaline particles can be obtained only when the amount of the particles does not exceed a certain limit, above which agglomeration of the primary particles takes place. This is the presumable mechanism for the results that the electric conductivity of the distilled water was greatly increased when the content of the tourmaline particles in the rayon fibers is in the range from 0.05 to 2.0% by weight as is shown by Table 1 and by the curve I in FIG. 2.

Application Example

Thermographic skin-thermometry The thermographic skin-thermometry is a method in which the skin temperature is measured with an infrared camera of ultra-high sensitivity and the distribution of the skin temperature is expressed in a chart called a thermogram by using 10 different colors corresponding to the respective temperature ranges.

Three mattresses for bed sheeting, referred to as the mattresses A, B and C, were prepared from different rayon fibers including the tourmaline-containing rayon fibers of sample No. 3 prepared and tested in Example 1, the tourmaline-containing rayon fibers of sample No. 14 prepared and tested in Example 2 and rayon fibers of sample No. 11 containing no tourmaline particles, respectively. Each of the mattresses A, B and C was spread on a bed and a healthy adult person as a subject lay thereon with his face facing upwardly. The skin temperature of the subjects was monitored by the thermography to find that the temperature of their feet was increased by 1.1° C. and by 0.6° C. on the mattresses A and B, respectively, during and after lying indicating invigoration of the subcutaneous blood circulation while no temperature increase was detected on the feet of the subject lying on the mattress C.

The above described experimental results lead to a conclusion that the tourmaline particles contained in the rayon fibers have an effect to increase the temperature of human skin by the invigorating effect on the subcutaneous blood circulation and this effect depends on the particle size of the tourmaline particles in good coincidence with the results by the measurement of electric conductivity of water obtained in Examples 1 and 2. In other words, measurement of the conductivity of water conducted in Examples 1 and 2 would provide good indices on the invigorating activity of the tourmaline-containing fibers on the living body cells to cause promotion of the subcutaneous blood circulation.

EXAMPLE 3

Figure 3:
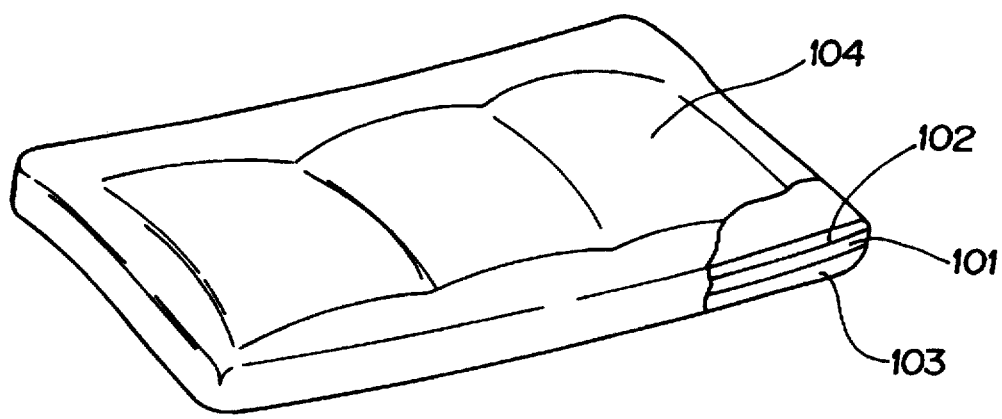
FIG. 3 is a perspective view of the mattress of the invention as partially cut open.
Figure 4:
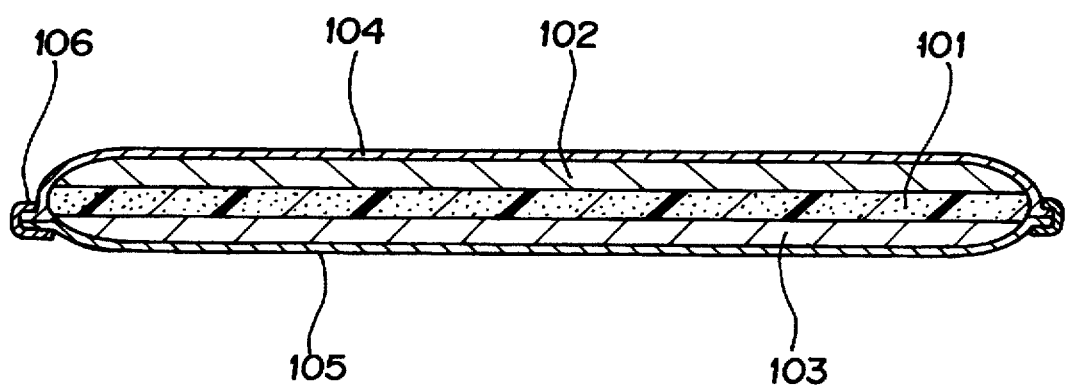
FIG. 4 is a vertical cross sectional view of the mattress according to the invention.

A mattress having a batting layer of tourmaline-containing rayon fibers illustrated in FIGS. 3 and 4 by a perspective view partially cut open and a vertical cross sectional view, respectively, was prepared. The batting layer 101 was a non-woven fabric sheet of a 50:50 mixture of polyester fibers and tourmaline-containing rayon fibers which contained 1% by weight of particles of tourmaline having a particle diameter not exceeding 1 μm and 5% by weight of fine particles of a ceramic material capable of emitting far-infrared light having a particle diameter not exceeding 1 μm.

The batting layer 101 was sandwiched between a pair of wadding layers 102,103 of polyester staples, of which the upper wadding layer 102 contained an insecticide and antibacterial agent. The thus formed three-layered mattress was enveloped in a fabric bag consisting of the top sheet 104 of a stretch-woven fabric of mixed fibers of 47% rayon, 50% polyester and 3% polyurethane and a bottom sheet 105 of polyester fibers conforming the three-layered mattress by providing hems 106 therearound.

By virtue of the batting layer consisting of the tourmaline-containing fibers, the mattress having the above described laminar structure had an invigorating effect on living body cells and invigoration and a stimulating effect on the living body tissues so as to improve the blood circulation in the living body lying thereon. The simple structure of the layered mattress enables whole laundering so as to keep cleanness and a sanitary condition conveniently. The sanitariness of the mattress can be further promoted by the use of the wadding layer 102 containing an insecticide and an antibacterial agent.

EXAMPLE 4

Figure 5:
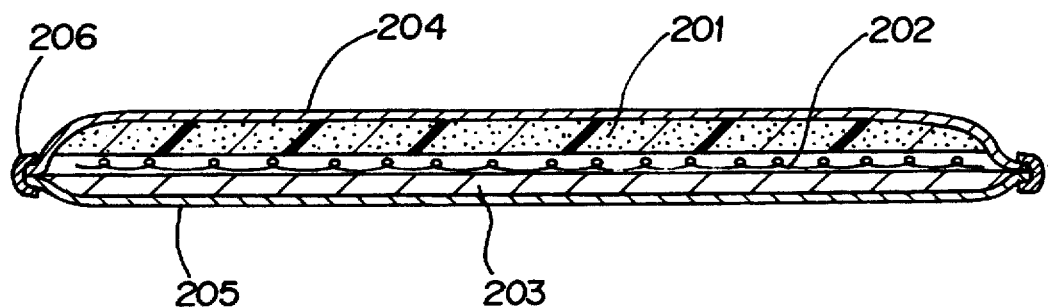
FIGS. 5 and 6 are each a vertical cross sectional view of the mattress according to the invention in a different embodiment having a built-in heater.

A mattress of a layered structure having a batting layer of tourmaline-containing fibers and having a built-in electric heater was prepared, of which the vertical cross sectional view is illustrated in FIG. 5. The batting layer 201 was a non-woven fabric sheet of a 50:50 mixture of polyester fibers and tourmaline-containing rayon fibers containing 2% by weight of tourmaline particles having a particle diameter not exceeding 1 µm and 10% by weight of ceramic particles having a particle diameter not exceeding 1 µm. A layer of electric heater 202, of which the resistance wires were sheathed with a thin sheet of polyurethane fibers, was sandwiched between the above mentioned tourmaline-containing batting layer 201 and an interlining layer 203 of polyester felt to ensure stability of the form of the mattress. The distribution of the resistance wire for the heater 202 was not uniform over the whole area of the mattress but was dense in the areas coming into contact with the lower half of the body of the person lying on the mattress. The thus formed layered structure was enveloped in a bag consisting of the top sheet 204 of a Jacquard-woven polyester cloth and a bottom sheet 205 of a polyester cloth containing interwoven aluminum filaments, which served to enhance the reflectivity to far-infrared light toward the top surface, in conformity with the layered structure by providing hems 206 therearound.

The mattress having the above described layered structure had an invigorating effect on the living body cells of a person lying on the mattress by stimulating the living body tissue to improve the blood circulation of the person lying thereon. This advantageous effect was more remarkable by the synergism with the heating means by the heater 202. Namely, the amount of active electrons released from the tourmaline particles is greatly increased by the pyroelectric effect of the tourmaline particles when heated by the heater 202. This health-promoting effect was further enhanced by the aluminum filaments interwoven in the bottom covering cloth 205 due to the increase in the reflection of far-infrared light toward the top surface.

EXAMPLE 5

Figure 6:
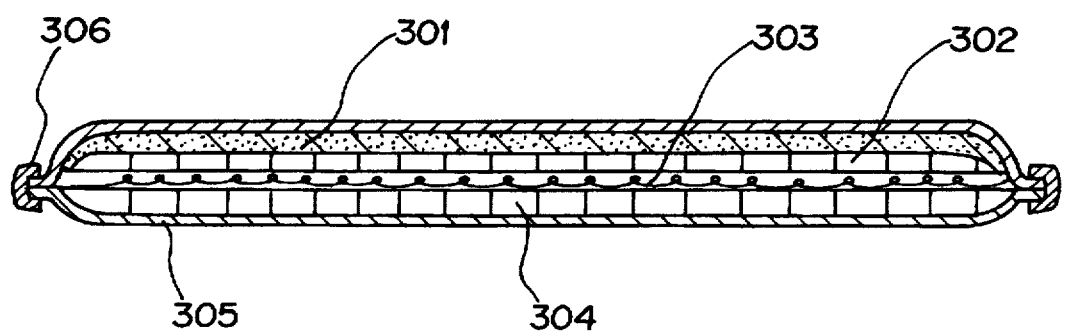

A mattress according to the invention was prepared, of which a vertical cross sectional view is illustrated in FIG. 6. Thus, a batting layer 301, which was a non-woven fabric sheet of a 30:70 mixture of tourmaline-containing rayon fibers and polyester fibers was mounted on a layered structure consisting of an electric heater layer 303 of resistance wires sheathed with a thin polyurethane fiber sheet sandwiched between two three-dimensional fabric sheets of honeycomb structure 302,304 described later. The thus obtained layered structure was enveloped in a bag 305 of polyester cloths having a form in conformity with the layered structure with hems 306 therearound.

Figure 7A:
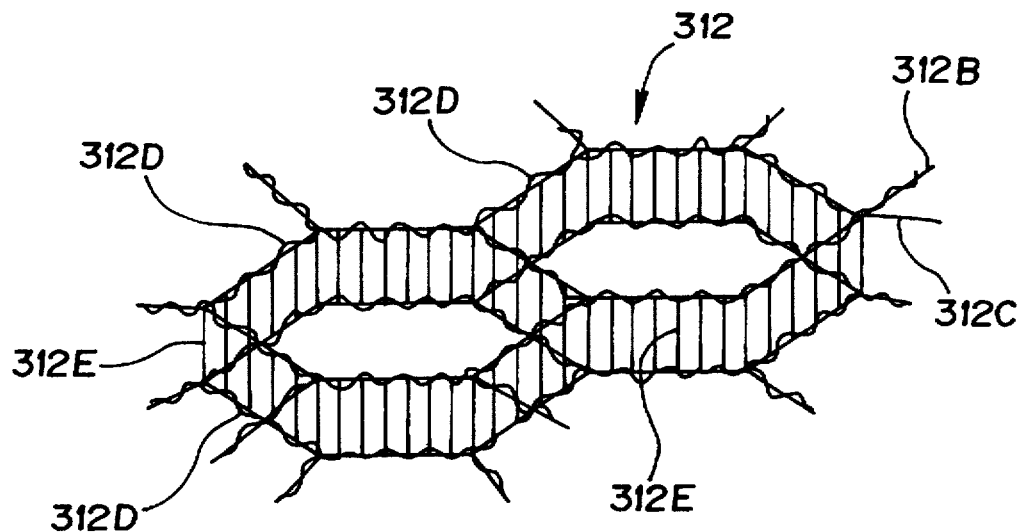
FIG. 7A is a perspective view of a three-dimensional honeycomb structure knit body.

FIG. 7A is an enlarged perspective view of the above mentioned three-dimensional sheet 302 or 304 in FIG. 6 having a honeycomb structure 312 consisting of hexagonal honeycomb cellular layers 312D. This honeycomb structure 312 is formed from 35% polyester fibers and 65% cotton fibers, though not particularly limitative thereto. The hexagonal honeycomb cellular layer 312D is formed from the thread 312B and the thread 312C intertwisted together. Two layers of the hexagonal cells 312D are put one on the other and they are laced up with a somewhat thicker lacing thread 312E having elasticity. The lacing thread 312E is preferably a monofilament of nylon. The unit cells forming the three-dimensional structure is not limited to hexagonal ones illustrated in FIG. 7A but can be octagonal or tetragonal.

Figure 7B:
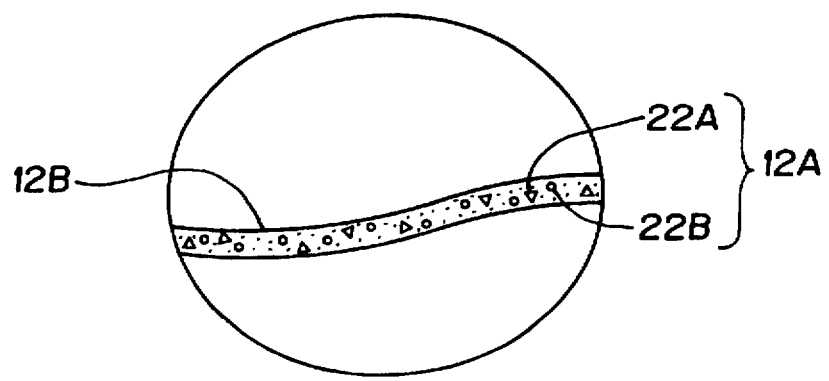
FIG. 7B is a microscopic sketch of a single fiber containing fine particles dispersed therein.

When the layers 302 and 304 sandwiching the heater layer 303 in FIG. 6 have such a three-dimensional honeycomb structure 312, the mattress of the invention is imparted with excellent air permeability so as to prevent propagation of microorganisms which may be responsible for the occurrence of bedsores on the patient's body lying thereon prolongedly together with the synergistic effect of the good elastic resilience to effect dispersion of the body weight over a wide area so as to improve blood circulation. When the three-dimensional honeycomb structure 312 is formed in the above described manner, the mattress is suitable for whole laundering in an electric washer and rapidly dried by virtue of the excellent air permeability. When the three-dimensional honeycomb structure 312 is formed from fibers containing fine tourmaline particles, furthermore, active electrons can be emitted from the honeycomb structure 312. FIG. 7B is a microscopic sketch of the fiber 12B containing particles 12A including the particles of tourmaline 22A and particles of another mineral or ceramic 22B. Fibers containing these particles can be used for the preparation of the three-dimensional honeycomb structure illustrated in FIGS. 10 to 13 by a schematic cross sectional view.

EXAMPLE 6

FIG. 8 is a perspective view of the mattress 400 according to the invention consisting of an intermediate layer 420 with a built-in heater sandwiched between an upper fabric sheet 410 and a lower fabric sheet 430 in the form of a bag closable and openable by means of a zipper 440 so that the intermediate layer with a built-in heater can be demounted therefrom so as to facilitate laundering of the bag consisting of the upper and lower fabric sheets 410,430 using a conventional electric washer.

Figure 9:
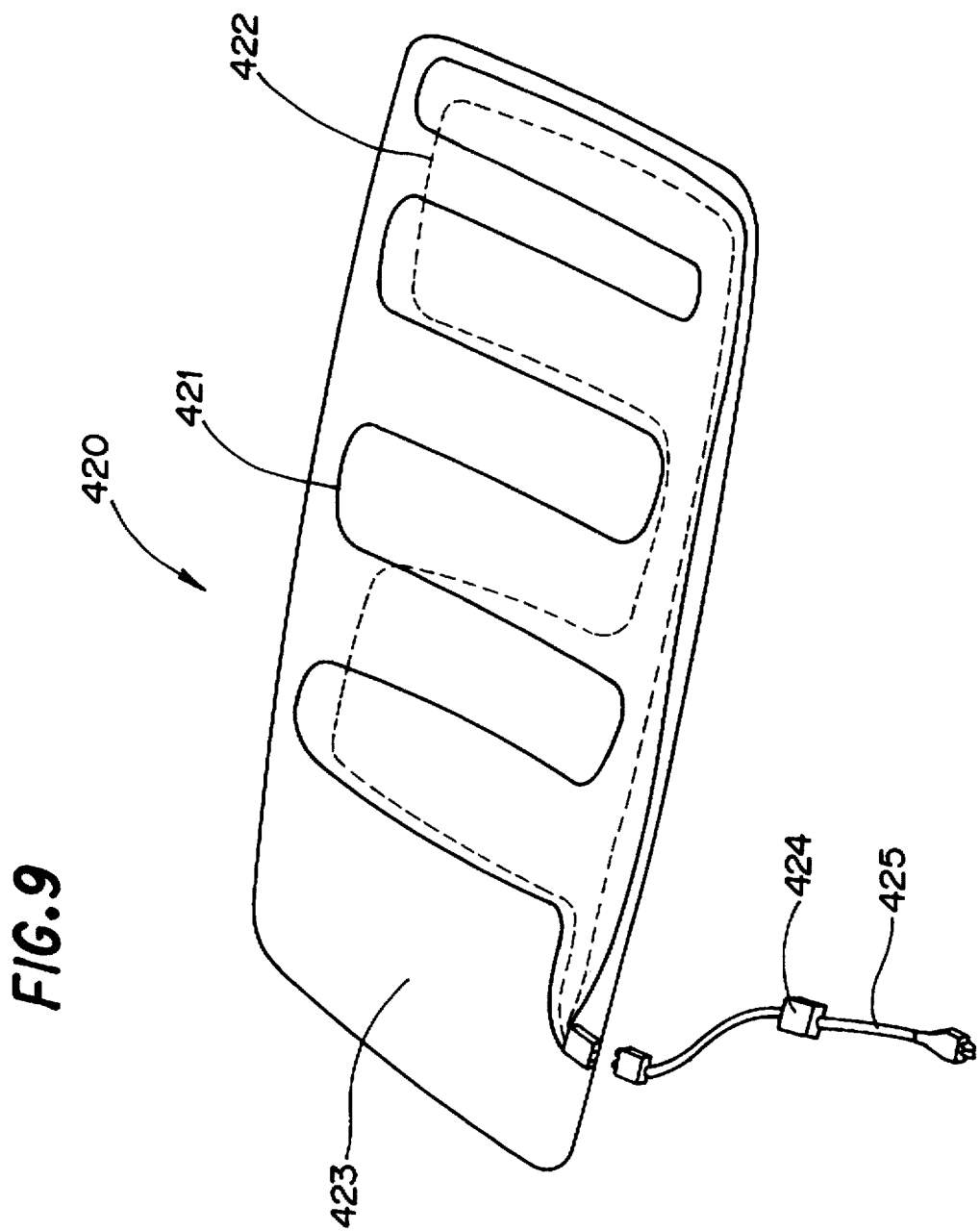
FIG. 9 is a perspective view of the intermediate layer with a built-in heater taken out of the mattress shown in FIG. 8.

FIG. 9 is a schematic perspective view of the intermediate layer 420 in FIG. 8, as taken out of the bag of the upper and lower fabric sheets 410,430, which consists of a heater wire 421, sensor wire 422, heater blanket 423 to hold the heater wire 421 and sensor wire 422 at the respective positions, temperature controller 424 to serve as a thermostatting means of the heater and power-supply cord 425.

Figure 10:
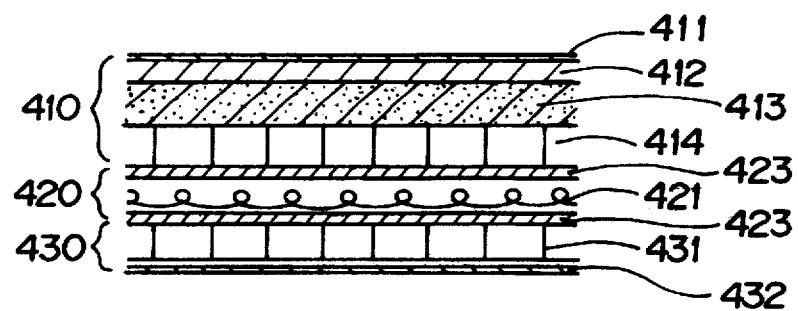
FIGS. 10 to 13 are each a vertical cross sectional view of a mattress according to the invention comprising two honeycomb layers and an intermediate layer with a built-in heater.

FIG. 10 is a cross sectional view of the mattress illustrated in FIG. 8. As is illustrated there, the upper fabric sheet 410 has a layered composite structure consisting of a surface cloth 411 of, for example, polyester fibers, resin-finished wadding layer 412 mainly consisting of polyester fibers, non-woven fabric layer 413 containing fine particles of tourmaline and three-dimensional honeycomb layer 414 while the lower fabric sheet 430 consists of a lower surface cloth 432 of, for example, polyester fibers and three-dimensional honeycomb layer 431.

The mattress having the above described structure gives a very soft feeling of cushioning to the person lying thereon by virtue of the resin-finished wadding layer 412 along with the living-body invigorating effect by the non-woven fabric layer 413 containing fine tourmaline particles capable of emitting active electrons and emitting far-infrared light. The intermediate heater layer 420 consists of a heater wire 421 and a stay cloth 423 supporting the heater wire 421 in the position.

EXAMPLE 7

Figure 11:
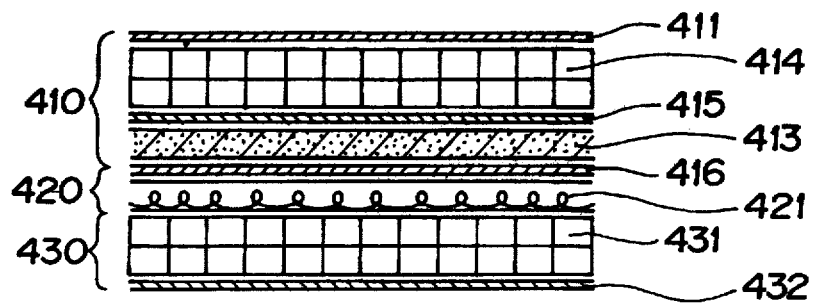

FIG. 11 is a cross sectional view showing the layered structure of the inventive mattress in another embodiment having somewhat increased rigidity and improved air permeability of the mattress, in which the non-woven fabric layer 413 containing tourmaline particles as sandwiched between two stay cloths 415,416 is sandwiched as a batting layer between the heater layer 420 and the upper fabric sheet 410 consisting of a double-honeycomb layer 414 and surface cloth 411. The lower fabric sheet 430 consists of a lower surface cloth 432 and a double-honeycomb layer 431.

EXAMPLE 8

Figure 12:
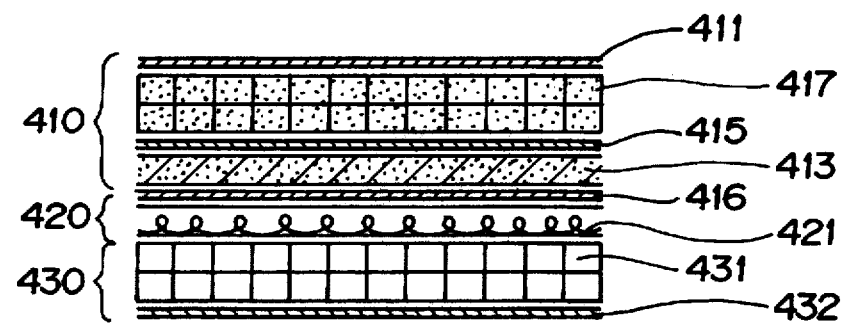

FIG. 12 is a cross sectional view of the inventive mattress of a still different embodiment, in which the fine particles of tourmaline are contained not only in the non-woven fabric layer 413 but also in the fibers forming the upper double-honeycomb layer 417 so that the effectiveness of the active electrons released from the tourmaline particles can be enhanced as compared with the mattress illustrated in FIG. 11 because of the proximity of the tourmaline-containing layer to the human body lying on the mattress.

EXAMPLE 9

Figure 13:
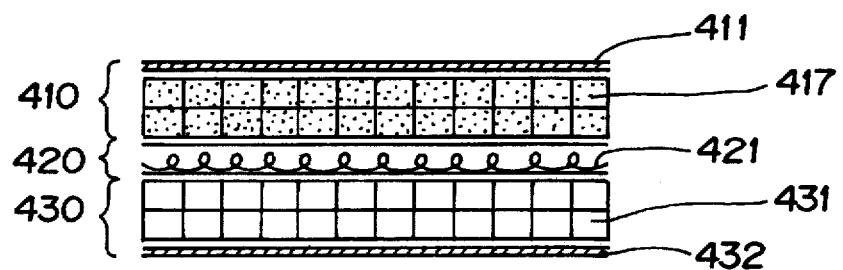

FIG. 13 is a cross sectional view of the inventive mattress according to a further different embodiment, in which, different from the mattress illustrated in FIG. 12, the batting layer of the non-woven fabric 413 is omitted so as to further improve the air permeability of the mattress so that the bedsore-preventing effect of the mattress can be enhanced so much.

What is claimed is:

1. A fabric mattress having a layered structure which comprises:

(a) an upper fabric layer;

(b) a lower fabric layer having a three dimensional steric structure; and (c) an intermediate fabric layer sandwiched between the upper and lower fabric layers comprising a heater blanket supporting a heater wire, said intermediate layer being readily separable from said upper and lower fabric layers, tourmaline particles being contained essentially in fibers forming said upper layer and optionally in fibers forming said other layers, said tourmaline particles having a particle diameter not exceeding 0.2 μm and an average particle diameter not exceeding 0.1 μm and the amount of tourmaline particles contained in the fibers being in the range of from 0.05 to 2.0% by weight based on the weight of said fibers without tourmaline.

2. The fabric mattress having a layered structure as claimed in claim 1 in which the fibers forming at least a part of the layers (a), (b) and (c) further contain particles of a far infrared emitting ceramic material.

3. The fabric mattress having a layered structure as claimed in claim 2 in which the far infrared emitting ceramic material is selected from the group consisting of alumina, cordierite, β-spodumen, zirconia, zircon, magnesia, aluminum titanate and oxides of transition metals.

4. The fabric mattress having a layered structure as claimed in claim 2 in which the amount of the particles of the far infrared emitting ceramic material does not exceed 10% by weight based on the fibers.

5. The fabric mattress having a layered structure as claimed in claim 1 in which the fiber containing particles of tourmaline is selected from fibers of rayon, cellulose acetate, polyester, polyurethane, polyamide, polyvinyl chloride, polyvinyl alcohol and polyacrylonitrile.

6. The fabric mattress having a layered structure as claimed in claim 5 in which the fiber containing particles of tourmaline is a fiber of rayon.

7. The fabric mattress having a layered structure as claimed in claim 1 in which the amount of the particles of the tourmaline contained in the fibers is in the range from 0.05% to 7.0% by weight based on the fibers.

8. The fabric mattress having a layered structure as claimed in claim 1 in which the intermediate layer comprises a sheet of non-woven fabric formed from fibers containing particles of tourmaline.

9. The fabric mattress having a layered structure as claimed in claim 1 in which the intermediate layer is a composite sheet comprising a sheet of non-woven fabric formed from fibers containing particles of tourmaline, a sheet having a three-dimensionally knit structure and a heater blanket supporting a heater wire.

10. The fabric mattress having a layered structure as claimed in claim 9 in which the three-dimensionally knit structure is a three dimensionally knit honeycomb structure.

11. The fabric mattress having a layered structure as claimed in claim 1 in which the upper fabric layer comprises a sheet having a three-dimensionally knit structure.

12. The fabric mattress having a layered structure as claimed in claim 11 in which the sheet having a three-dimensionally knit structure comprised in the upper fabric layer is formed from fibers containing particles of the tourmaline.

13. The fabric mattress having a layered structure as claimed in claim 1 in which the lower fabric layer comprises a sheet having a three-dimensionally knit structure.

14. The fabric mattress having a layered structure as claimed in claim 13, wherein the three dimensional knit structure is a honeycomb structure.

* * * * *